United States Patent
Carlyon et al.

(10) Patent No.: US 9,713,573 B2
(45) Date of Patent: Jul. 25, 2017

(54) BLUNT TIP VIAL ACCESS CANNULA AND METHOD FOR MANUFACTURE

(71) Applicant: Covidien LP, Mansfield, MA (US)

(72) Inventors: James L. Carlyon, Farmington, MO (US); Gregory Steube, St. Charles, MO (US)

(73) Assignee: Covidien LP, Mansfield, MA (US)

( * ) Notice: Subject to any disclaimer, the term of this patent is extended or adjusted under 35 U.S.C. 154(b) by 857 days.

(21) Appl. No.: 13/764,158

(22) Filed: Feb. 11, 2013

(65) Prior Publication Data
US 2014/0053953 A1 Feb. 27, 2014

Related U.S. Application Data

(62) Division of application No. 12/164,657, filed on Jun. 30, 2008, now Pat. No. 8,382,722.

(51) Int. Cl.
*A61J 1/20* (2006.01)
*B21G 1/08* (2006.01)
(Continued)

(52) U.S. Cl.
CPC ............ *A61J 1/2096* (2013.01); *B21D 51/16* (2013.01); *B21G 1/08* (2013.01); *A61J 1/201* (2015.05);
(Continued)

(58) Field of Classification Search
CPC .......... A61M 5/3286; A61M 2205/195; A61M 5/3291; A61M 5/162; A61M 5/158;
(Continued)

(56) References Cited

U.S. PATENT DOCUMENTS

| 2,541,272 A | 2/1951 | Murphy |
| 2,746,455 A | 5/1956 | Abel |

(Continued)

FOREIGN PATENT DOCUMENTS

WO 2004030731 A2 4/2004

OTHER PUBLICATIONS

Office action issued Mar. 24, 2010 in related U.S. Appl. No. 12/164,657 now issued as U.S. Pat. No. 8,382,722, 11 pgs.

(Continued)

*Primary Examiner* — Bhisma Mehta
*Assistant Examiner* — Brandy S Lee
(74) *Attorney, Agent, or Firm* — Blaine A. Page, Esq.

(57) ABSTRACT

A method of manufacturing a metal cannula is disclosed. The method includes the step of providing a metal cannula having a longitudinal axis and defining a fluid channel. Next, the metal cannula is pressed to substantially close the fluid channel and define a first segment and a second segment. In a next step, the metal cannula is cut to separate the first segment from the second segment of the metal cannula. Each of the first and second segments have a pressed edge. The pressed edge substantially seals the fluid channel and has two pressed corners. Afterwards, each of the pressed corners are cut from the pressed edge of the first segment to define a pair of side openings and a distal blunt edge on the first segment. The side openings are in fluid communication with the fluid channel.

22 Claims, 5 Drawing Sheets

(51) Int. Cl.
*B21D 51/16* (2006.01)
*A61M 5/178* (2006.01)
*A61M 5/32* (2006.01)

(52) U.S. Cl.
CPC ......... *A61J 2200/10* (2013.01); *A61M 5/1782* (2013.01); *A61M 5/3291* (2013.01); *A61M 2205/6081* (2013.01); *Y10T 29/49826* (2015.01); *Y10T 83/0429* (2015.04)

(58) Field of Classification Search
CPC .... A61M 5/32; A61M 1/3659; A61M 1/3661; A61M 2005/3267; A61M 2025/0031; A61M 2025/0037; A61M 2025/0073; A61M 2039/082; A61M 2205/583; A61M 2205/59; A61M 2205/6081; A61M 5/1782; B21G 1/08; B21G 1/006; B21G 1/00; A61J 1/201; A61J 1/20; A61J 1/2075; A61J 1/2096; A61J 2200/10; B21D 51/16; Y10T 29/49826; Y10T 83/0429
USPC .................................................. 604/274, 272
See application file for complete search history.

(56) References Cited

U.S. PATENT DOCUMENTS

| | | | |
|---|---|---|---|
| 2,752,919 A | | 7/1956 | Gabriel |
| 2,954,768 A | | 10/1960 | Hamilton |
| 3,181,336 A | * | 5/1965 | Schofield .................. 72/340 |
| 3,831,814 A | | 8/1974 | Butler |
| 3,906,932 A | * | 9/1975 | Ayres .................. A61M 5/162 222/80 |
| 4,072,041 A | * | 2/1978 | Hoffman et al. ............... 72/416 |
| 4,276,880 A | * | 7/1981 | Malmin ......................... 604/28 |
| 4,387,879 A | | 6/1983 | Tauschinski |
| 4,675,020 A | | 6/1987 | McPhee |
| 4,710,180 A | | 12/1987 | Johnson |
| 4,723,955 A | | 2/1988 | Vaillancourt |
| 4,838,877 A | | 6/1989 | Massau |
| 4,842,591 A | | 6/1989 | Luther |
| 5,059,172 A | | 10/1991 | Sutherland et al. |
| 5,167,642 A | | 12/1992 | Fowles |
| 5,188,620 A | | 2/1993 | Jepson et al. |
| 5,211,638 A | | 5/1993 | Dudar et al. |
| 5,470,327 A | | 11/1995 | Helgren et al. |
| 5,584,819 A | | 12/1996 | Kopfer |
| 5,746,733 A | | 5/1998 | Capaccio et al. |
| 5,755,696 A | | 5/1998 | Caizza |
| 5,820,621 A | | 10/1998 | Yale et al. |
| 5,832,971 A | | 11/1998 | Yale et al. |
| 5,833,674 A | | 11/1998 | Turnbull et al. |
| 5,919,182 A | | 7/1999 | Avallone |
| 5,928,162 A | | 7/1999 | Giurtino et al. |
| 5,928,215 A | | 7/1999 | Caizza et al. |
| 5,976,115 A | | 11/1999 | Parris et al. |
| 6,206,858 B1 | | 3/2001 | Kempen et al. |
| 6,358,236 B1 | | 3/2002 | DeFoggi et al. |
| 6,394,979 B1 | | 5/2002 | Sharp et al. |
| 6,447,498 B1 | | 9/2002 | Jepson et al. |
| 6,610,041 B2 | | 8/2003 | Daubert et al. |
| 6,637,470 B2 | | 10/2003 | Reihl et al. |
| 6,715,520 B2 | | 4/2004 | Andreasson et al. |
| 6,832,994 B2 | | 12/2004 | Niedospial, Jr. et al. |
| 6,875,205 B2 | | 4/2005 | Leinsing |
| 6,901,975 B2 | | 6/2005 | Aramata et al. |
| 6,921,395 B2 | | 7/2005 | Carano et al. |
| 8,382,722 B2 | | 2/2013 | Carlyon et al. |
| 2004/0024354 A1 | | 2/2004 | Reynolds |
| 2005/0096698 A1 | * | 5/2005 | Lederman .................... 606/222 |
| 2006/0200095 A1 | * | 9/2006 | Steube .................. A61J 1/2096 604/272 |
| 2006/0287639 A1 | * | 12/2006 | Sharp .................... A61J 1/2096 604/415 |

OTHER PUBLICATIONS

Response filed Jul. 20, 2010 to Office action dated Mar. 24, 2010 regarding related U.S. Appl. No. 12/164,657 now issued as U.S. Pat. No. 8,382,722, 20 pgs.
Final Office action issued Sep. 21, 2010 in related U.S. Appl. No. 12/164,657 now issued as U.S. Pat. No. 8,382,722, 6 pgs.
Response filed Nov. 22, 2010 to Final Office action dated Sep. 21, 2010 regarding related U.S. Appl. No. 12/164,657 now issued as U.S. Pat. No. 8,382,722, 16 pgs.
Office action issued Apr. 18, 2012 in related U.S. Appl. No. 12/164,657 now issued as U.S. Pat. No. 8,382,722, 6 pgs.
Response filed Jul. 18, 2012 to Final Office action dated Apr. 18, 2012 regarding related U.S. Appl. No. 12/164,657 now issued as U.S. Pat. No. 8,382,722, 4 pgs.

* cited by examiner

BLUNT TIP VIAL ACCESS CANNULA AND METHOD FOR MANUFACTURE

CROSS REFERENCE TO RELATED APPLICATION

This application is a divisional of and claims priority to co-pending U.S. patent application Ser. No. 12/164,657, filed Jun. 30, 2008, which is hereby incorporated by reference in its entirety.

BACKGROUND

Technical Field

The present disclosure relates to cannula assemblies and their method of manufacture. More particularly, the present disclosure relates to blunt tip cannula assemblies for accessing a vial and their method of manufacture.

Description of Related Art

In the medical field, fluid transfer devices, particularly, vial access devices are commonly used to draw medicaments from medical vials in order to fill syringes. Medical vials are well known in the medical field and typically include a pierceable septum and a body defining a reservoir for containing a medicinal fluid. Vial access devices typically include a syringe having a syringe body, a plunger assembly, and a needle or cannula hub assembly. Typically, the cannula assembly includes a hollow needle or cannula configured to pierce a septum of a vial and a needle hub which can be removably attached to the syringe body. The needle or cannula can be formed from metal or plastic. After medical fluid has been withdrawn from a medical vial into the syringe, the needle hub assembly can be removed from the syringe body, such that, an intravenous catheter or a syringe needle may be connected to the filled syringe to deliver the medicament into a patient.

There are certain medicaments which are stored in vials that should not be physically disturbed, e.g., by inverting the vial, while accessing the medicament in the vial. Current medical practice requires the use of a relatively long cannula assembly, e.g., about 1.5 inches, to access the bottom portion of such a vial. Although, plastic needles are desirable because they present less of a risk of needle-stick injury, plastic needles are weaker than metal needles and generally can be no longer than about ½ inch in length before their diameters become unreasonably large. Thus, plastic needles cannot be used to access such vials because of their weakness.

Accordingly, a continuing need exists in the medical arts for a blunt tip cannula assembly which can access vials greater than ½ inch in depth, while at the same time being less likely to cause needle stick injuries.

SUMMARY

A method of manufacturing a metal cannula is disclosed. The method includes the step of providing a metal cannula having a longitudinal axis and defining a fluid channel. Next, the metal cannula is pressed in an orthogonal direction in relation to the longitudinal axis of the metal cannula at a specified location to substantially close the fluid channel and define a first segment and a second segment. The metal cannula is pressed by a pressing technique selected from the group consisting of rolling, shearing, crimping, and pressing. In a next step, the metal cannula is cut at the specified location to separate the first segment from the second segment of the metal cannula. Each of the first and second segments have a pressed edge. The pressed edge substantially seals the fluid channel and has two pressed corners.

Afterwards, each of the pressed corners are cut from the pressed edge of the first segment to define a pair of side openings and a distal blunt edge on the first segment. The side openings are in fluid communication with the fluid channel. The side openings are defined by side facets, which are finished by a machining technique selected from the group consisting of grinding, cutting, and polishing. In one embodiment, the cutting step includes cutting the edge corners at different angles or radii.

An additional step includes attaching the proximal end of the blunt metal tip cannula to a hub assembly to form a vial access cannula. The metal cannula is coupled to the distal end of the hub assembly by a fastening technique selected from the group consisting of gluing, snap-fitting, crimping, press-fitting, and molding. The metal cannula can be colored by staining or anodizing.

In embodiments, the step of providing a metal cannula includes providing a metal cannula having an extended length. The metal cannula can be pressed at a multiplicity of locations to define a multiplicity of segments. Afterwards, the metal cannula is cut at the multiplicity of locations to separate the multiplicity of segments. Each segment includes a pressed edge on each side having two pressed corners, where each pressed edge substantially seals the fluid channel. Next, the pressed corners are cut from the pressed edges of a single segment to define a pair of side openings and a distal blunt edge on each end of the single segment. The side opening is in fluid communication with the fluid channel. Next, the single segment is cut at a desired midpoint to form two separate blunt metal tip cannulae. Each blunt metal tip cannula includes an open proximal end and a closed distal blunt edge having at least one side opening.

In another embodiment, a method of manufacturing a metal cannula is disclosed. The method includes the steps of providing a metal cannula having a fluid channel defined therein and defining a longitudinal axis therethrough. Next, a u-shaped notch is cut at the distal end of the metal cannula. The u-shaped notch is formed by a cutting technique selected from the group consisting of grinding, laser cutting, electrical discharge machining, photo-chemical machining, and water jetting. The u-shaped notch defines a first segment and a second segment, where the first and second segments have opposed distal tips. The opposed tips of first segment and second segment are cut in an acute angle in relation to a longitudinal axis of the metal cannula. Next, the opposed tips of the first and second segments are arranged in a crimping device. The crimping device may be a metal die having a first part and a second part. The first and second parts of the metal die define a shape desired to form a blunt metal tip.

Next, the first and second segments are crimped to form a blunt metal tip. The blunt metal tip has a substantially closed distal end and defines a pair of side openings. The side openings are defined by side facets. The side facets are finished by a machining technique selected from the group consisting of grinding, cutting, and polishing The side facets may be cut at different angles or radii In embodiments, the proximal end of the blunt metal tip cannula is attached to a hub assembly to form a vial access cannula. The metal cannula is coupled to the distal end of the hub assembly by a fastening technique selected from the group consisting of gluing, snap-fitting, crimping, press-fitting, and molding. A further step may include coloring the metal cannula by staining or anodizing.

A vial access device prepared by a process is disclosed. The process includes an initial step of providing a metal cannula, which has a longitudinal axis and defines a fluid channel. Next, the metal cannula is pressed in an orthogonal direction in relation to the longitudinal axis of the metal cannula at a specified location to substantially close the fluid channel and define a first segment and a second segment. Next, the metal cannula is cut at the specified location to separate the first segment from the second segment of the metal cannula. Each of the first and second segments has a pressed edge, where the pressed edge substantially seals the fluid channel and has two pressed corners. In the next step, each of the pressed corners is cut from the pressed edge of the first segment to define a pair of side openings and a distal blunt edge on the first segment. The side openings are in fluid communication with the fluid channel. The proximal end of the blunt metal tip cannula is attached to a hub assembly to form a vial access cannula.

A vial access device prepared by a process is disclosed. The process includes the steps of: providing a metal cannula having a fluid channel defined therein and defining a longitudinal axis therethrough; cutting a u-shaped notch at the distal end of the metal cannula, the u-shaped notch defining a first segment and a second segment, each of the first and second segments having opposed distal tips; cutting the opposed tips of first segment and second segment in an acute angle in relation to a longitudinal axis of the metal cannula; arranging the opposed tips of the first and second segments in a crimping device; and crimping the first and second segments to form a blunt metal tip, the blunt metal tip having a substantially closed distal end and defining a pair of side openings. In embodiments, an additional step includes attaching the proximal end of the blunt metal tip cannula to a hub assembly to form a vial access cannula.

A vial access device is disclosed which includes a metal cannula having a longitudinal axis and defining a fluid channel. The metal cannula is pressed at a first specified location in an orthogonal direction in relation to the longitudinal axis to substantially close the fluid channel and define a first segment. The metal cannula is cut at the first specified location to separate the first segment from the remainder of the metal cannula, where the first segment has a pressed edge. The pressed edge substantially seals the fluid channel and has two pressed corners. The pressed corners are cut at a second specified location from the pressed edge of the first segment to define a pair of side openings and a distal blunt edge on the first segment. The side openings are in fluid communication with the fluid channel.

A vial access device is disclosed which includes a metal cannula having a fluid channel defined therein and defining a longitudinal axis therethrough. The vial access device further includes a u-shaped notch, which is cut at the distal end of the metal cannula. The u-shaped notch defines a first segment having a distal tip. The distal tip of first segment is cut at a specified location in an acute angle in relation to a longitudinal axis of the metal cannula. The first segment is crimped to form a blunt metal tip. The blunt metal tip has a substantially closed distal end and defines a pair of side openings. In embodiments, a proximal end of the blunt metal tip cannula is attached to a hub assembly to form a vial access cannula.

BRIEF DESCRIPTION OF THE DRAWINGS

Various embodiments of the presently disclosed blunt tip vial access cannula and its method of manufacture are disclosed herein with reference to the drawings, wherein.

DETAILED DESCRIPTION

Figure 1:
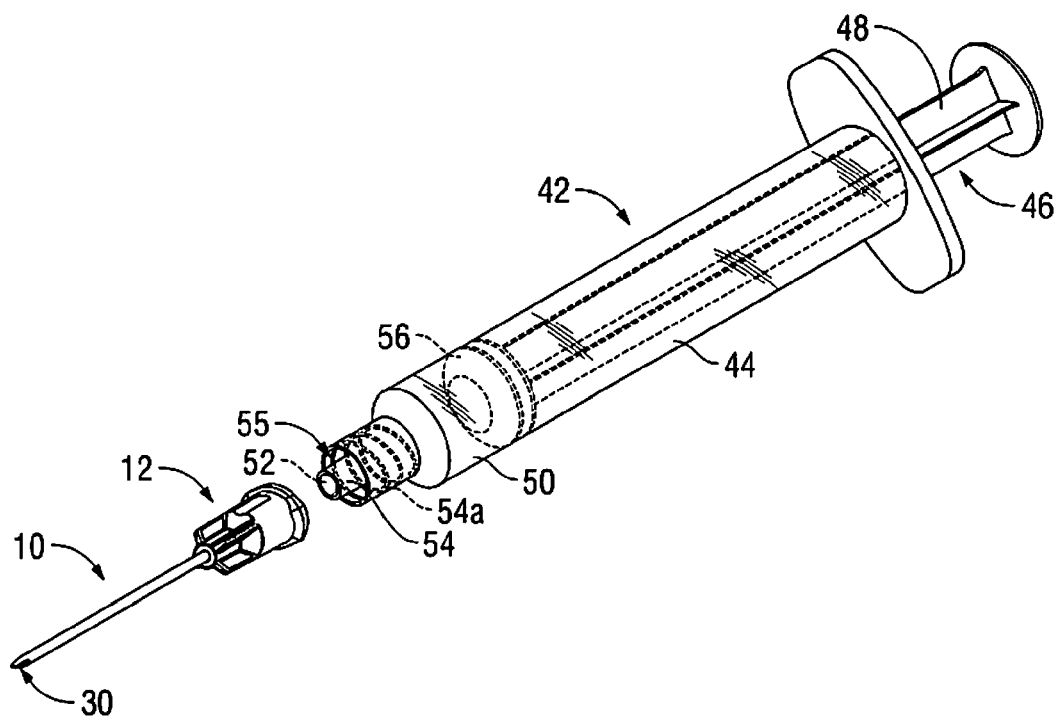
FIG. 1 is a partially exploded perspective view of one embodiment of the presently disclosed vial access cannula and a syringe assembly.

Embodiments of the presently disclosed vial access cannula will now be described in detail with reference to the drawings wherein like reference numerals designate identical or corresponding elements in each of the several views. In this description, the term proximal is generally used to indicate the relative nearness of a referenced item to a user of a device and the term distal is used to indicate the relative remoteness of a referenced item to a user of the device.

Figure 2:
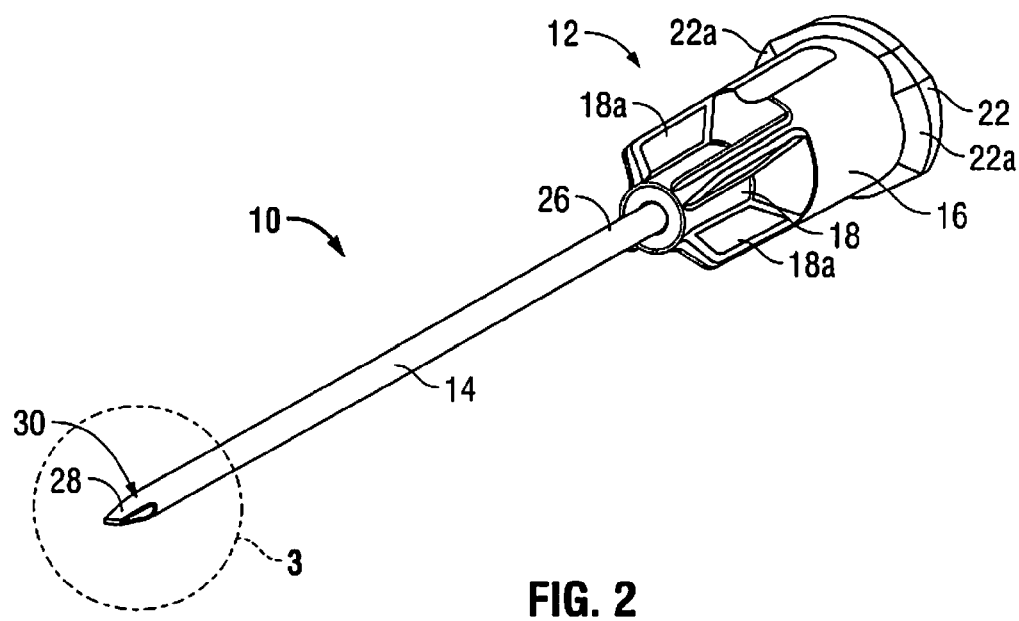
FIG. 2 is a perspective view of the vial access cannula shown in FIG. 1.
Figure 3:
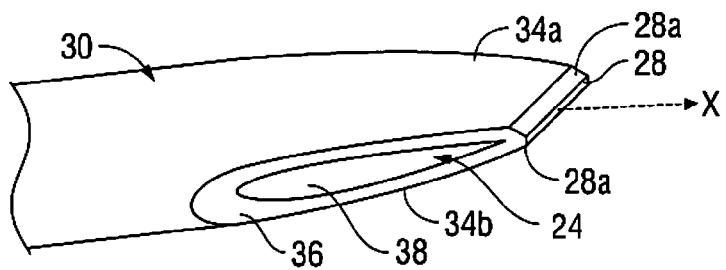
FIG. 3 is an enlarged view of the indicated area of detail shown in FIG. 2.
Figure 4:
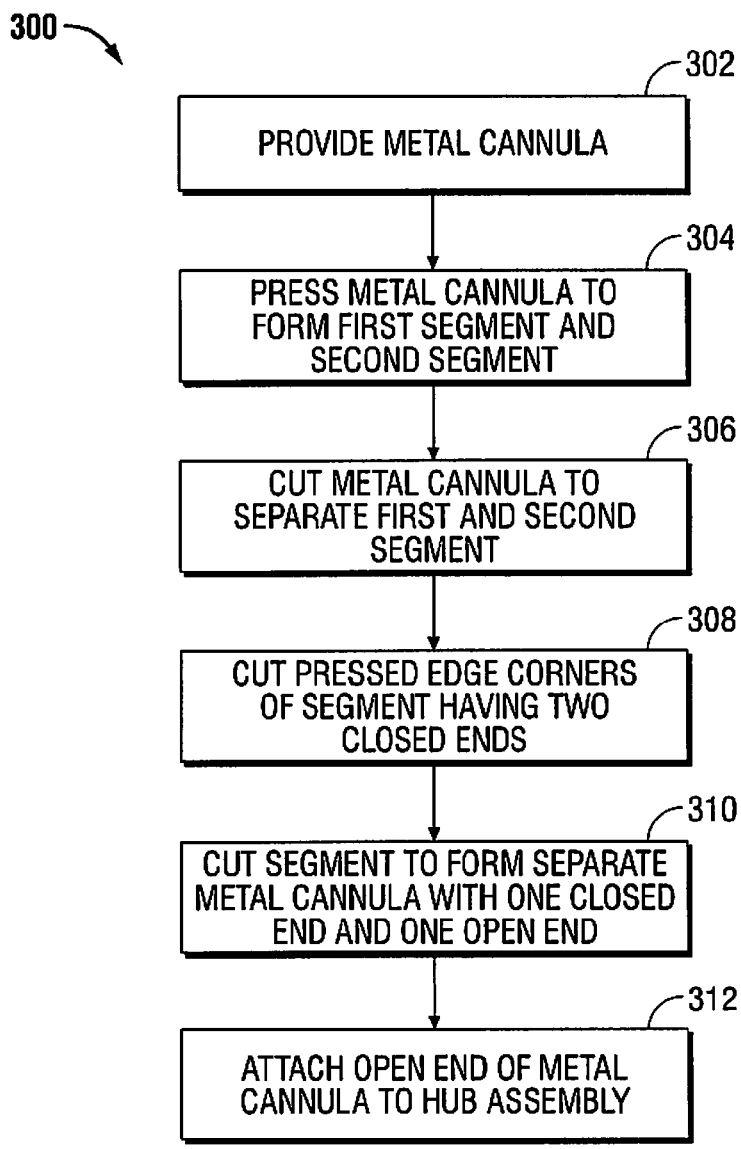
FIG. 4 is a flow chart showing the presently disclosed method of manufacture of the presently disclosed vial access cannula.

Referring initially to FIGS. 1 and 2, a vial access cannula 10 for use with a syringe assembly 42 is provided, which generally includes a needle hub assembly 12 and an elongated metal cannula 14 which has a blunt metal tip 30. The syringe assembly 42 includes a plunger assembly 46 and syringe body 44, that can be releasably connected to the needle hub assembly 12 via a luer-type connector. The hub member 12 includes a hub body portion 16 which is fixedly connected to a proximal end of the metal cannula 14 by crimping, welding, gluing, or the like. The metal cannula 14 terminates at a distal blunt cutting edge 28 on a distal end of the blunt metal tip 30. The blunt metal tip 30 includes a first segment 34a and a second segment 34b, which define side openings 38 (FIG. 3). All of the above-mentioned components will be discussed in greater detail below.

FIG. 1 illustrates a syringe assembly 42 having a syringe body 44 and a plunger assembly 46. Body 44 defines a fluid reservoir 50. Plunger assembly 46 includes a plunger rod 48 and a plunger head 56. Plunger head 56 is configured to be slidably received within reservoir 50 of syringe body 44 to deliver fluid from reservoir 50 to a fluid outlet 52, which is supported or formed on a distal end of body 44 in fluid communication with reservoir 50. Syringe assembly 42 also includes an annular coupling member 54, e.g., a luer-type connector, positioned partially about fluid outlet 52 as will discussed in further detail below.

Hub member 12 can be formed from a metal or plastic material, e.g., polypropylene, and includes a wide body portion 16, a narrow body portion 18 having tabs 18a, and a coupling member 22. The wide body portion 16 and the narrow body portion 18 are tubular and define a fluid channel (not shown) which is in fluid communication with a proximal end 26 of metal cannula 14. The metal cannula 14 defines a fluid channel 24 to allow fluid to pass from hub member 12 to the blunt metal tip 30. The tabs 18a of the narrow body portion 18 allow a user to firmly grip the hub assembly 12 when engaging or disengaging hub assembly 12 from the coupling member 54 of syringe assembly 42, as will be discussed in further detail below. In addition, the narrow body portion 18 is configured and dimensioned to receive a proximal end of metal cannula 14. The narrow body portion 18 is also positioned to engage a top portion of a vial to limit the depth of cannula 14 penetration through the septum of the vial (not shown).

As discussed above, the hub assembly 12 defines a fluid channel which extends from the metal cannula 14 and terminates in two side openings 38 of the blunt metal tip 30. It is envisioned that blunt metal tip 30 may terminate in one or more side openings 38. The vial access cannula 10 terminates at a distal blunt edge 28 of the blunt metal tip 30.

Turning now to FIG. 3, the blunt metal tip 30 includes cutting edge 28 having distal facets 28a and 28b. The distal cutting edge 28 is formed at the junction of the first segment 34a and second segment 34b of the blunt metal tip 30. The first and second segments 34a and 34b define side openings 38. The side facets 36 result when side openings 38 cut into first segment 34a and second segment 34b of the blunt metal tip 30. The side facets 36 are typically symmetrical on each of the lateral sides of the blunt metal tip 30 and are oriented orthogonal to the distal blunt edge 28. The manufacturing process of the blunt metal tip will be discussed in detail further below. The blunt metal tip 30, including the distal cutting edge 28 and the distal facets 28a and 28b, facilitate penetration of the septums or elastomeric stoppers medicinal vials. The purpose of the distal facets 28a and 28b is to facilitate smoother penetration of the blunt metal tip 30 of the metal cannula 14 through an elastomeric stopper. Cannulae without the distal facets 28a and 28b generally require the use of more force and are more prone to tear the vial stopper.

Referring back to FIGS. 1 and 2, coupling member 22 is configured to releasably engage annular coupling member 54 of syringe assembly 42 (FIG. 1) to releasably secure hub assembly 12 to syringe assembly 42. As illustrated, coupling member 22 may be a female luer-type coupling member which includes tabs 22a configured to rotatably engage threads 54a of annular coupling member 54 which is configured as a male luer-type coupling member. It is envisioned that a variety of different types of coupling members, for example, bayonet-type, snap-fit type or any other suitable coupling members could be used to couple hub assembly 12 to syringe assembly 42.

In order to attach the hub assembly 12 to the syringe assembly 42, coupling member 22 is inserted into an annular recess 55 defined between the annular coupling member 54 and fluid outlet 52 and rotated in relation to syringe assembly 42 in a first direction (clockwise) such that tabs 22a of coupling member 22 engage and interlock with threads 54a of annular coupling member 54. Hub assembly 12 can be detached from syringe assembly 42 by rotating the hub assembly 12 in a second direction (counter-clockwise direction) in relation to syringe assembly 42.

In use, the vial access cannula 10 is connected in fluid communication to the syringe assembly 42 in the manner described above. The user inserts the vial access cannula 10 into a medical vial (not shown) by piercing a pierceable septum with metal tip 30. The vial may contain any medicinal fluid appropriate for a particular medical procedure. The vial access cannula 10 may be inserted through the septum of the vial such that metal tip 30 engages a bottom portion of vial to retrieve the medicinal fluid. The user may then pull the plunger assembly 46 of the syringe assembly 42 and extract the appropriate amount of fluid necessary for the particular medical procedure.

The user may then remove the needle hub assembly 12 from the syringe assembly 42. Thereafter, syringe assembly 42 can be secured to a puncturing needle (not shown) or an indwelling catheter for directly injecting the medicinal fluid into a patient. Alternatively, other suitable cannula or needle hub assemblies may be secured to a distal end of the syringe (e.g., oral dose adapter, indwelling catheter, etc.) for delivery of the medicinal fluid from the syringe reservoir to the patient.

Figure 5:
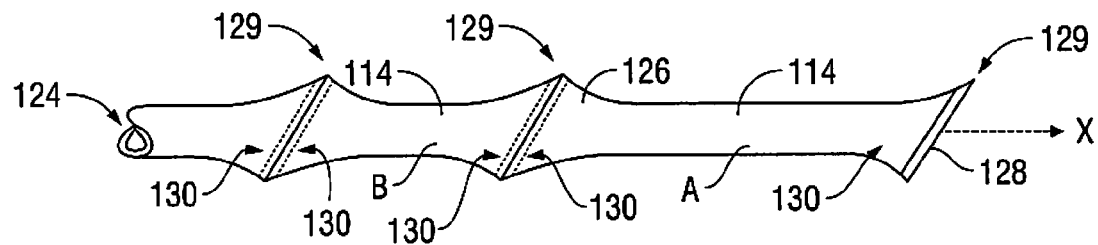
FIG. 5 is a side view of a cannula having a plurality of pressed locations during a first step of the presently disclosed method of manufacture of the presently disclosed vial access cannula.

In accordance with the present disclosure, a method of manufacturing a metal cannula 300 including a blunt metal tip for vial access cannula 10 will now be described. In an initial step 302, a metal cannula 114 is provided, which has an open-ended tubular configuration. In step 304, the metal cannula 114 is pressed in an orthogonal direction, in relation to a longitudinal axis "X" of the metal cannula 114. At least for a portion of the pressing process, the metal cannula is pressed at a specified pressed location 129. As a result, the metal cannula 114 is deformed into one or more pressed segments, e.g., a first segment A and a second segment B, as shown in FIG. 5. It is envisioned that metal cannula 114 is a continuous tube and each pressed location 129 is continuously pressed at an interval predetermined by the manufacturer. It also is envisioned that the metal cannula 114 may be color stained by anodizing or some other suitable coloring process. The color difference would enhance and help a user to distinguish the blunt metal cannula for accessing vials from a regular syringe for injection into patients. At the time of pressing, the cannula tube 114 is flattened at the pressed locations 129, thus substantially closing the cannula tube 114 at the pressed locations 129. Different techniques may be used to press the metal cannula 114, e.g., rolling, crimping, pressing, or the like. As will be appreciated, shears may be used to press and cut the cannula 114, simultaneously, at the pressed locations 129.

Figure 6:
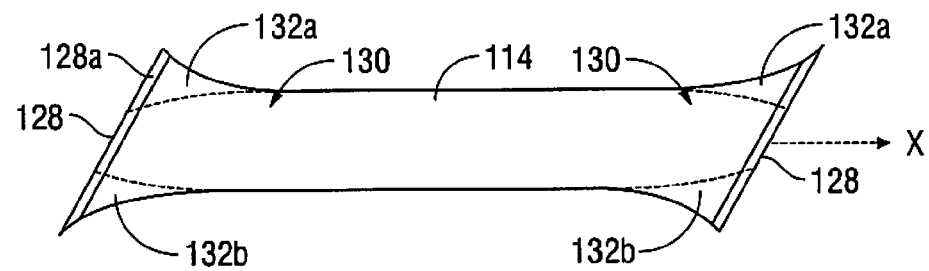
FIG. 6 is a side view of a segment of the presently disclosed vial access cannula during a second step of the presently disclosed method of manufacture.

In step 306, cut in an orthogonal, in relation to the longitudinal axis "X" of the metal cannula 114, is made. The cut along the pressed location 129 bisects the first segment A and the second segment B of cannula 114, thus separating first segment A from second segment B. As shown in FIG. 6, the cutting step results in a cannula tube 114 having two closed distal ends 128 and a pair of pressed edge corners 132. At this point of the manufacturing process, facets 128a and 128b may be added (i.e., grinded, cut, polished, etc.) into the distal end 128 of cannula tube 114.

Figure 7:
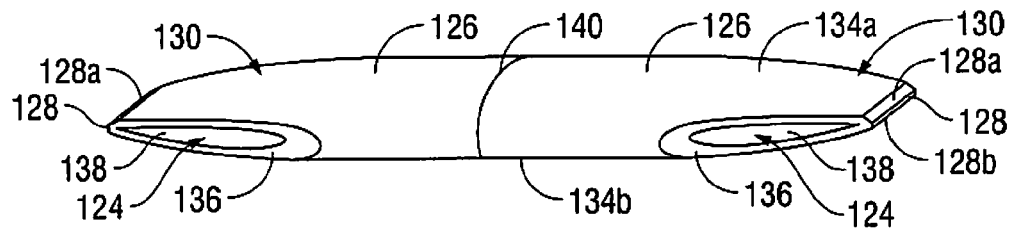
FIG. 7 is a perspective view of the segment of the vial access cannula shown in FIG. 6 after a third step of the presently disclosed method of manufacture.
Figure 8:
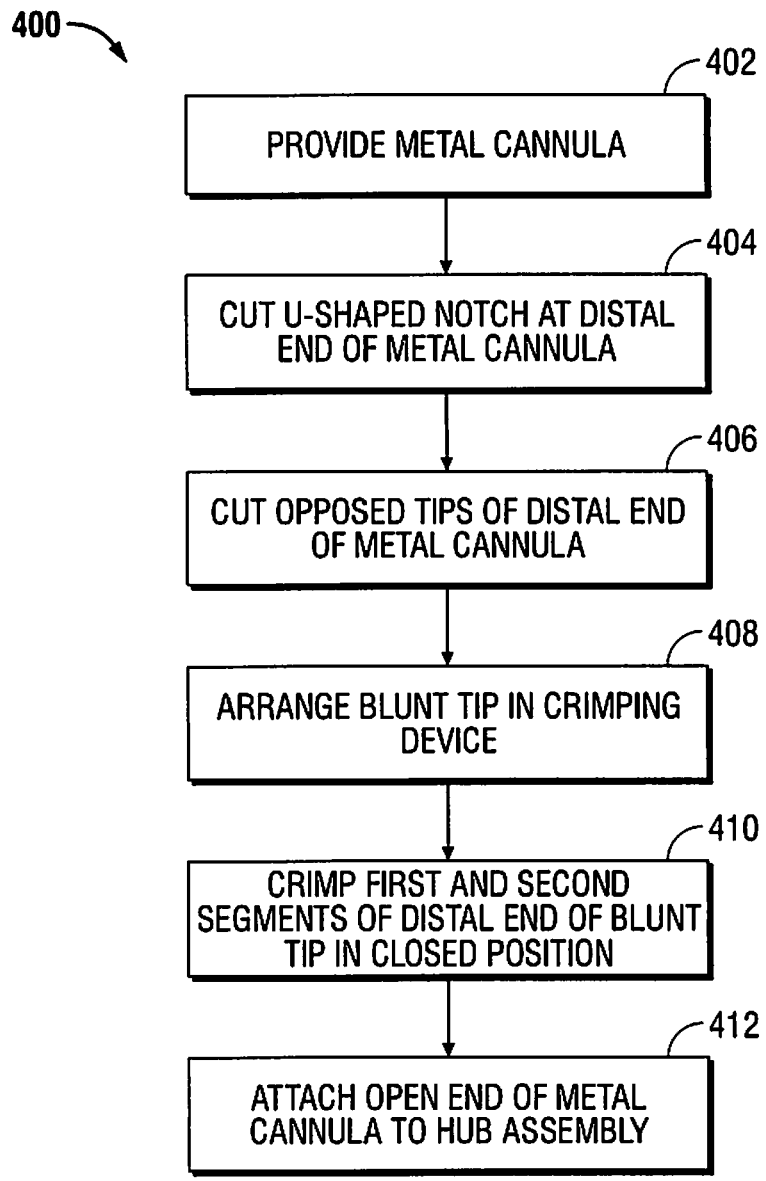
FIG. 8 is a flow chart showing an alternative embodiment of the presently disclosed method of manufacture.

In step 308, each pressed edge corner 132 is cut at an acute angle in relation to the longitudinal axis of the metal cannula 114. It is envisioned that both edge corners 132a and 132b are cut at the same angle as the other such that each side of the metal cannula 114 defines a mirror image of the other side. Alternatively, it is envisioned that edge corners 132a and 132b may be cut at different angles or radii. After the edge corners 132a and 132b are cut off the distal end 128 of cannula 114, as depicted in FIG. 7, the cut results in cannula 114 having a facet 136 and an opening 138 on each side that the edge corners 132a and 132b were cut. The edge corners 132a and 132b are cut at a pre-determined location. As it will be appreciated by one skilled in the art, the desired cut location and size will be determined in light of the size and angle of the inlet ports 138 and facets 136 required. For example, cutting the edge corners 132a and 132b at a position farther from the corner point of edge corners 132a and 132b results in a larger inlet port, whereas, cutting the edge corners 132a and 132b nearest to the corner point results in a smaller inlet port.

In step 310, the metal cannula is cut or dissected at a desired midpoint 140 to form two separate blunt metal tip cannulae 130, each having a substantially distal closed end 128 and a proximal open end 126. In step 312, the proximal end 126 of the finished blunt metal tip cannula 130 is attached to a hub assembly to form a vial access cannula as described above. Any suitable attaching means may be used to attach blunt metal tip cannula 130 to the hub assembly (e.g., bonding, welding, crimping, press fitment, insert molding, etc.)

Figure 9:
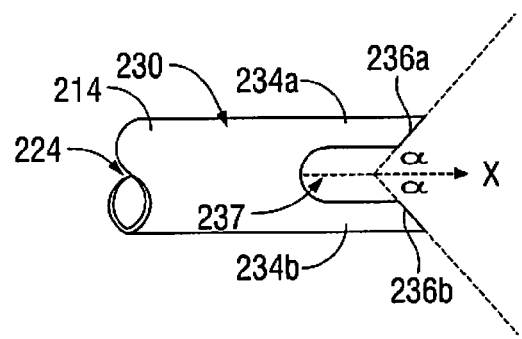
FIG. 9 is a side view of a distal end of a cannula prior to formation of the blunt tip in the alternative embodiment of the presently disclosed method of manufacture.

In another embodiment of the present disclosure, a method of manufacturing a metal cannula 400 including a blunt metal tip will now be described. In an initial step 402, a metal cannula 214 is provided, which has a fluid channel 224 defined therein. In step 404, a first segment 234a and a second segment 234b of the metal cannula 214 are defined by cutting a u-shaped notch 237 on opposite sides of a distal end 230 of the metal cannula 214, as shown in FIG. 9. The cutting involved in this procedure may be performed by any suitable cutting means (e.g., grinding, laser cutting, electrical discharge machining, photo-chemical machining, water jet, etc.).

In step 406, opposed tips 236a and 236b of first segment 234a and second segment 234b are cut in an acute angle α in relation to a longitudinal axis "X" of the cannula 214. The acute angle α on each tip 236a and 236b should be selected so that when tips 236a and 236b are forced together, a substantially closed seal occurs. It is envisioned, that one skilled in the art may need to trim an appropriate amount of material of the metal cannula 114, in order to conform to a desired shape. For example, the manufacturer may grind or trim a specific angle onto tips 236a and 236b of the first and second segment 234a and 234b.

Figure 10:
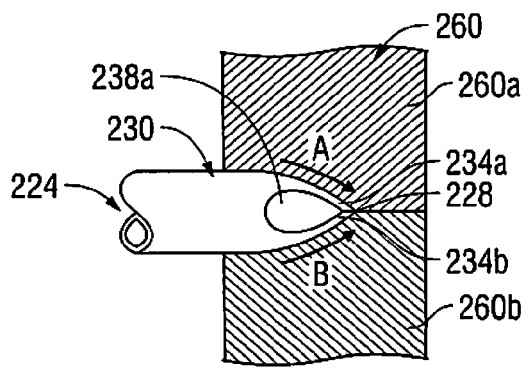
FIG. 10 is a side view of distal end of the cannula shown in FIG. 9 being crimped in a die.
Figure 11A:
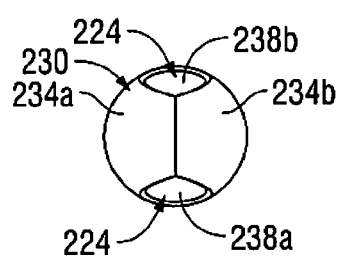
FIG. 11A is a front view of the crimped cannula shown in FIG. 10.
Figure 11B:
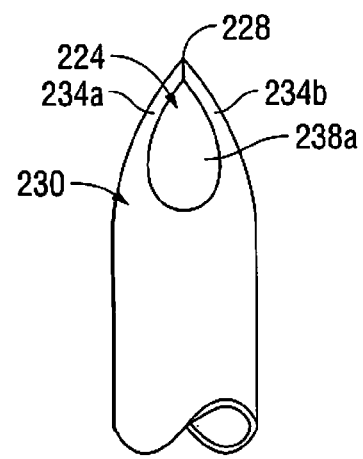
FIG. 11B is a side view of the crimped cannula shown in FIG. 10.

In step 408, the distal end 230 is arranged in a crimping device (e.g., a metal die), as shown in FIG. 10. The metal die 260 includes a first part 260a and a second part 260b, when assembled, first and second part 260a and 260b of the metal die 260 form the shape desired for forming the distal end 230 into a blunt metal tip. In step 410, the first and second segments 234a and 234b of distal end 230 are crimped (i.e., pressed into the die with adequate force) together into a closed position. As explicitly shown in FIG. 10, when the distal end 230 is crimped into the closed position, the first segment 234a is forced in a direction indicated by arrow "A" and the second segment 234b is forced in a direction indicated by arrow "B". The distal closed end 228 is defined when the angled tips 236a and 236b are in contact with each other. FIGS. 11A and 11B depict the side openings 238a and 238b, which are defined when the angled tips 236a and 236b contact each other. At this point of the manufacturing process, facets 228a and 228b may be added (i.e., grinded, cut, polished, etc.) into the distal end 228 of cannula tube 214.

In addition, step 408 may include a mandrel to be used in combination with the above-mentioned crimping device. The mandrel is configured to aid the crimping device by supporting the metal cannula 114 during crimping. A mandrel may also be used to support the metal cannula 114 in conjunction with a single die or punch.

In step 412, the proximal end 226 of the finished metal cannula 214 is attached to a hub assembly resulting in a blunt tip vial access cannula, as previously discussed and shown in FIG. 2. Any suitable attaching means may be used to attach metal cannula 214 to the hub assembly (e.g., bonding, welding, crimping, press fitment, insert molding, etc.)

It is contemplated that in the above-referenced methods of manufacturing a metal cannula, 300 and 400, the sequences of steps may be performed in any suitable sequence. For example, in the method of manufacturing a metal cannula 300, step 308, where each pressed edge corner 132 is cut at an acute angle, may precede step 306, wherein the metal cannula 114 is cut to separate the first segment A and the second segment B.

Although the illustrative embodiments of the present disclosure have been described herein with reference to the accompanying drawings, it is to be understood that the disclosure is not limited to those precise embodiments, and that various other changes and modifications may be effect therein by one skilled in the art without departing from the scope or spirit of the disclosure.

What is claimed is:

1. A method of manufacturing a metal connula, comprising the steps of:
    providing a metal cannula having a fluid channel defined therein and defining a central longitudinal axis therethrough;
    cutting a u-shaped notch defining a first segment and a second segment, each of the first and second segments having opposed distal tips;
    cutting the opposed distal tips of the first segment and the second segment in an acute angle in relation to the central longitudinal axis of the metal cannula forming respective first and second planar faces that face the central longitudinal axis;
    arranging the opposed distal tips of the first and second segments in a crimping device; and
    crimping the first and second segments to form a blunt metal tip, the blunt metal tip having a substantially closed distal end and defining a pair of side openings.

2. The method according to claim 1, comprising a further step of attaching a proximal end of the metal cannula to a hub assembly to form a vial access cannula.

3. The method according to claim 2, wherein the metal cannula is coupled to a distal end of the hub assembly by a fastening technique selected from the group consisting of gluing, snap-fitting, crimping, press-fitting, and molding.

4. The method according to claim 1, comprising a further step of coloring the metal cannula by staining or anodizing.

5. The method according to claim 1, wherein the step of cutting a u-shaped notch is performed by a cutting technique selected from the group consisting of grinding, laser cutting, electrical discharge machining and water jetting.

6. The method according to claim 1, wherein the step of cutting the opposed distal tips includes a cut made in an angle in relation to the central longitudinal axis of the metal cannula.

7. The method according to claim 1, wherein the step of crimping the first and second segments includes a metal die having a first part and a second part, the first and second parts of the metal die defining a shape desired to form the blunt metal tip.

8. The method according to claim 1, wherein the side openings are defined by side facets.

9. The method according to claim 8, wherein the side facets are finished by a machining technique selected from the group consisting of grinding, cutting, and polishing.

10. The method according to claim 1, wherein cutting the opposed distal tips comprises cutting the tip of the first segment to form the first planar face that is skewed with respect to the central longitudinal axis of the metal cannula and cutting the tip of the second segment to form the second planar face that is skewed with respect to the central longitudinal axis of the metal cannula, wherein the first planar face and the second planar face are not parallel to each other, and
wherein crimping the first and second segments comprises bringing the first and second planar faces into engagement with each other such that the first and second planar faces are generally parallel to each other.

11. The method according to claim 1, wherein cutting the opposed distal tips comprises cutting an axially outward-facing end surface of each of the first and second segments lying in a plane perpendicular to the central longitudinal axis of the metal cannula so that the end surface faces toward the central longitudinal axis and makes an acute angle in relation to the central longitudinal axis of the metal cannula.

12. The method according to claim 1, wherein the acute angle on each distal tip is selected so that when the opposed distal tips are forced together, a substantially closed seal occurs.

13. A vial access device prepared by a process comprising the steps of:
providing, a metal cannula having a fluid channel defined therein and defining a central longitudinal axis therethrough;
cutting a u-shaped notch at a distal end of the metal cannula, the u-shaped notch defining a first segment and a second segment, each of the first and second segments having opposed distal tips;
cutting the opposed distal tips of the first segment and the second segment in an acute angle in relation to the central longitudinal axis of the metal cannula forming respective first and second planar faces that face the central longitudinal axis;
arranging the opposed distal tips of the first and second segments in a crimping device; and
crimping the first and second segments to form a blunt metal tip, the blunt metal tip having a substantially closed distal end and defining a pair of side openings.

14. The vial access device prepared by a process according to claim 13, comprising a further step of attaching a proximal end of the metal cannula to a hub assembly to form a vial access cannula.

15. The vial access device prepared by a process according to claim 14, wherein the metal cannula is coupled to a distal end of the hub assembly by a fastening technique selected from the group consisting of gluing, snap-fitting, crimping, press-fitting, and molding.

16. The vial access device prepared by a process according to claim 13, comprising a further step of coloring the metal cannula by staining or anodizing.

17. The vial access device prepared by a process according to claim 13, wherein the step of cutting a u-shaped notch is performed by a cutting technique selected from the group consisting of grinding, laser cutting, electrical discharge machining, and water jetting.

18. The vial access device prepared by a process according to claim 13, wherein the step of cutting the opposed distal tips includes a cut made in an angle in relation to the central longitudinal axis of the metal cannula.

19. The vial access device prepared by a process according to claim 13, wherein the step of crimping the first and second segments includes a metal die having a first part and a second part, the first and second parts of the metal die defining a shape desired to form the blunt metal tip.

20. The vial access device prepared by a process according to claim 13, wherein the side openings are defined by side facets.

21. The vial access device prepared by a process according to claim 20, wherein the side facets are finished by a machining technique selected from the group consisting of grinding, cutting, and polishing.

22. The vial access device prepared according to the method of claim 13, wherein the acute angle on each distal tip is selected so that when the opposed distal tips are forced together, a substantially closed seal occurs.

* * * * *